US011826055B2

(12) United States Patent
Zille et al.

(10) Patent No.: US 11,826,055 B2
(45) Date of Patent: Nov. 28, 2023

(54) SURGICAL GUIDES INCLUDING REMOVABLE STRUTS

(71) Applicant: OsteoMed LLC, Addison, TX (US)

(72) Inventors: Devid R. Zille, Addison, TX (US); Johanna Scheeh, Euless, TX (US)

(73) Assignee: OsteoMed LLC, Addison, TX (US)

( * ) Notice: Subject to any disclaimer, the term of this patent is extended or adjusted under 35 U.S.C. 154(b) by 378 days.

(21) Appl. No.: 17/073,641

(22) Filed: Oct. 19, 2020

(65) Prior Publication Data

US 2021/0113216 A1    Apr. 22, 2021

Related U.S. Application Data

(60) Provisional application No. 62/916,347, filed on Oct. 17, 2019.

(51) Int. Cl.
*A61B 17/15*    (2006.01)
*A61B 17/80*    (2006.01)
*A61B 17/56*    (2006.01)

(52) U.S. Cl.
CPC ........ *A61B 17/151* (2013.01); *A61B 17/8071* (2013.01); *A61B 2017/568* (2013.01)

(58) Field of Classification Search
CPC ............................ A61B 17/151; A61B 17/176
See application file for complete search history.

(56) References Cited

U.S. PATENT DOCUMENTS

2013/0310838 A1\* 11/2013 Kurtz ................... A61B 17/157
606/88
2020/0315803 A1    10/2020 Zille

OTHER PUBLICATIONS

U.S. Appl. No. 17/006,603, Zille.

\* cited by examiner

*Primary Examiner* — Olivia C Chang
(74) *Attorney, Agent, or Firm* — K&L Gates LLP

(57) ABSTRACT

The present application describes various embodiments of guides that include one or more removable struts. The guides may include at least two guide portions that are connected to one another via at least one strut. In embodiments, the at least one strut may be designed such that it could be disconnected from at least one of the guide portions. The removable feature of the strut allows a surgeon to perform an osteotomy procedure by using the cutting slots and other relevant markings defined on the secured portions of the guide.

20 Claims, 12 Drawing Sheets

US 11,826,055 B2

SURGICAL GUIDES INCLUDING REMOVABLE STRUTS

CROSS REFERENCE TO RELATED APPLICATIONS

The present application claims priority to U.S. Provisional Application No. 62/916,347 filed Oct. 17, 2019 and entitled "SURGICAL GUIDES INCLUDING REMOVABLE STRUTS," the disclosure of which is incorporated by reference herein in its entirety.

TECHNICAL FIELD

The present disclosure generally relates to surgical guides used during osteotomy procedures. In particular, the disclosure describes surgical guides including removable struts and a method for manufacturing surgical guides including removable struts.

BACKGROUND

An osteotomy procedure is generally performed to correct bone-related defects and/or abnormalities. The procedure may include a surgical operation where a surgeon (e.g., an orthopedic surgeon) operates on a bone to bring change to its underlying structure (e.g., changing its length or alignment). An illustrative osteotomy procedure may include surgically cutting or dividing the tibia bone (or a portion thereof) and then shifting the divided ends to change the alignment of the tibia bone. Another illustrative osteotomy procedure may include resecting a segment of a mandible and repositioning the resected segment (or a portion thereof) to a preferred location to achieve a desired shape of the lower facial region.

Surgeons may employ different types of techniques to perform osteotomy procedures. Some surgeons use a freehand technique where they perform the procedure manually, without the aid of guiding instruments. However, the freehand technique is technically demanding, can lead to inaccuracies (e.g., inaccurate cuts), and may result in undesired surgical outcomes, such as fractures, gap formation, angulation, inadequate length of excision, misalignment of the implant against the bone, and poor coaptation of the junction surface. To prevent these undesired surgical outcomes and to improve precision, some surgeons use devices, such as surgical cutting guides, during the procedures. A surgical cutting guide (hereinafter referred to as "guide") is a stencil-like customized tool made from a sterilizable material. In some cases, the guides include cutting slots and other relevant markings defined on them that assist surgeons in sawing and/or drilling the bone in the desired direction and for the desired length, thereby improving the quality of the procedure.

Some guides include one or more permanent struts that 1) connect together different portions of the guide, 2) facilitate positioning of the different portions at desired locations over a biological structure, and 3) resist forces that would otherwise displace the different portions from their desired positions and/or bring the different portions towards each other. Referring to FIG. 1(a), a three dimensional (3D) rendered image 100 of a portion of mandible 102 is shown. FIG. 1(a) depicts guide 104 placed on lower portion of mandible 102. Guide 104 includes left portion 106, right portion 108, and strut 110 that is permanently attached to the left and right portions 106 and 108, respectively. The left and right portions 106 and 108 may be designed to temporarily clutch guide 104—without using any surgical screws/wires—to the underlying mandible 102. Both left portion 106 and right portion 108 may also define apertures 112 and 114 that allow guide 104 to fixedly secure itself to the mandible 102 using surgical screws and/or wires.

A series of steps that may be performed by a surgeon during an illustrative osteotomy procedure on mandible 102 using guide 104 are now described. The surgeon may first expose a desired portion of mandible 102 that is to be operated. The surgeon may then position and affix guide 104 to the desired portion of mandible 102 using one or more surgical fixating devices (e.g., surgical screws and/or wires). After that, the surgeon may draw or create osteotomy lines on the operated bone using appropriate tools and then remove guide 104 in order to perform the osteotomy procedure (e.g., resect the bone along the osteotomy lines). The surgeon typically removes guide 108 to perform the procedure because strut 110 visually blocks the osteotomy lines and interferes with the surgeon's ability to resect along the osteotomy lines. To illustrate, referring to FIG. 1(b), the 3D rendered image 100 is depicted from a different perspective. In a scenario where the surgeon desires to resect bone 102 along the YZ plane, strut 110 blocks the line of resection and interferes during surgery. Accordingly, the surgeon removes guide 104 from the bone to perform the osteotomy procedure without any interference. However, resecting the bone by cutting along osteotomy lines, i.e., not using cutting slots and other relevant markings defined on the guide 104, may lead to inaccuracies (e.g., inaccurate resection of the bone). Further, the surgeon loses valuable time by first affixing and then removing guide 104 from mandible 102.

SUMMARY

The present application describes various embodiments of guides that include one or more removable struts. The guides described herein include at least two guide portions that are connected to one another via at least one strut. In embodiments, the at least one strut may be designed such that it could be disconnected from at least one of the guide portions. In embodiments, the at least one strut may be designed such that it could be disconnected from the at least two guide portions. The removable feature of the strut eliminates the interferences discussed above and allows the surgeon to perform the osteotomy procedure by using the cutting slots and other relevant markings defined on the secured portions of the guide.

In embodiments, the at least one strut may be designed such that it could be disconnected from at least one of the guide portions before or after, for example, the at least one of the guide portions is secured to the underlying biological structure. In embodiments, the at least one strut may be designed such that it could be disconnected from at least two guide portions before or after the at least two guide portions are secured to the underlying biological structure. In embodiments, the at least one strut may be designed such that it could be disconnected from at least one of the guide portions before or after the at least two guide portions are secured to the underlying biological structure. For example, the at least one strut may disconnect from one secured guide portion and be permanently connected to the other secured guide portion. The side of the at least one strut that is permanent connected to the other secured guide portion, in embodiments, may be rotatable.

In embodiments, at least one guide portion of the guide may be secured with the underlying biological structure using one or more surgical fixation devices, such as surgical screws, surgical wires, and the like. In embodiments, at least two guide portions may be secured with the underlying biological structure using surgical fixation devices. The underlying biological structure, in some cases, may include anatomical landmarks—which may be points or locations of interest on the human body or the skeletal system where guides can be placed in a fitted manner and/or attached (or latched) without being explicitly secured using fixating devices (e.g., wires or surgical screws). In such cases, before at least one strut may be disconnected, at least one portion of the guide may be secured at the anatomical landmark without using any fixating devices. In embodiments, at least one guide portion may be secured with the underlying biological structure using one or more surgical fixation devices and another guide portion may be secured with the underlying biological structure at the anatomical landmark with or without using any fixating devices. The at least one guide portion may be secured—either using fixation devices or around an anatomical landmark—as a standalone guide portion or with the at least one strut connected to it.

In aspects, the guides designed to include removable struts may be designed to enhance the overall functionality of the guide in that the guides may be designed to connect with different types/kinds of removable struts. This capability may allow the guide to perform more than one function during surgery. For example, a first one or more struts may allow the guide to perform the function of a cutting guide, whereas a second one or more struts may allow the guide to perform the function of a positioning guide. To illustrate, after securing the guide, the first one or more struts may be disconnected from the secured portions to eliminate the visual interference. This allows the surgeon to perform the osteotomy procedure using the cutting slots (and other relevant markings) defined on the guide and further allows the guide to function as a cutting guide. After performing the osteotomy procedure (e.g., after using the guide as a cutting guide), the surgeon may reposition the osteotomized biological structure with guide portions still secured upon them to a new position (that is different from the original position). The surgeon may connect the second one or more struts to the secured portions of the guide to reliably lock the osteotomized biological structure to the new position. Depending on the type of repositioning, the second one or more struts may be different in size (e.g., length) or have different slope (depending on the type of repositioning) and allow the guide to function as a positioning guide.

In aspects, the guides may be designed in accordance with the osteotomy procedure which the surgeon will be performing. In embodiments, the guides may further be designed to conform to the shape of the underlying biological structure. In embodiments, the guides may also be designed in accordance with one or more anatomical landmarks near the bone (or portion thereof) on which the surgeon wants to operate.

Some of the embodiments described herein provide for patient-specific guides. In embodiments, the guides may be custom designed individually for every patient according to the patient's anatomical model (which may be created from various medical imaging techniques (e.g., CT scans, MRI scans, and the like)). The present application also describes various embodiments of methods for manufacturing these guides. In some embodiments, the manufacturing process includes receiving patient imaging data, which is used to generate a model for the guide. This model is then used to produce the guide. The guides may be manufactured using 3D printing techniques, and the like.

The foregoing has outlined rather broadly the features and technical advantages of the embodiments in order that the detailed description of the embodiments that follows may be better understood. Additional features and advantages of the embodiments disclosed in this application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the embodiments in this application as set forth in the appended claims. The novel features which are believed to be characteristic of the embodiments, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding, reference is now made to the following descriptions taken in conjunction with the accompanying drawings, in which.

DETAILED DESCRIPTION

For the sake of illustration and clarity, this disclosure describes the guides that may be used during mandible-related osteotomy procedures. However, it should be appreciated that the disclosure is not intended to be limited to the examples and designs of guides used for mandible-related procedures, but is to be accorded the widest scope consistent with the principles and novel features of the guides with removable struts, as disclosed ahead. Thus, the description ahead is provided to enable any person of ordinary skill in the art to make or use the disclosure. Various modifications to the disclosure will be readily apparent to those skilled in the art, and the generic principles of the use and manufacturing of the guides defined herein may be applied to other variations as well.

Figure 1A:
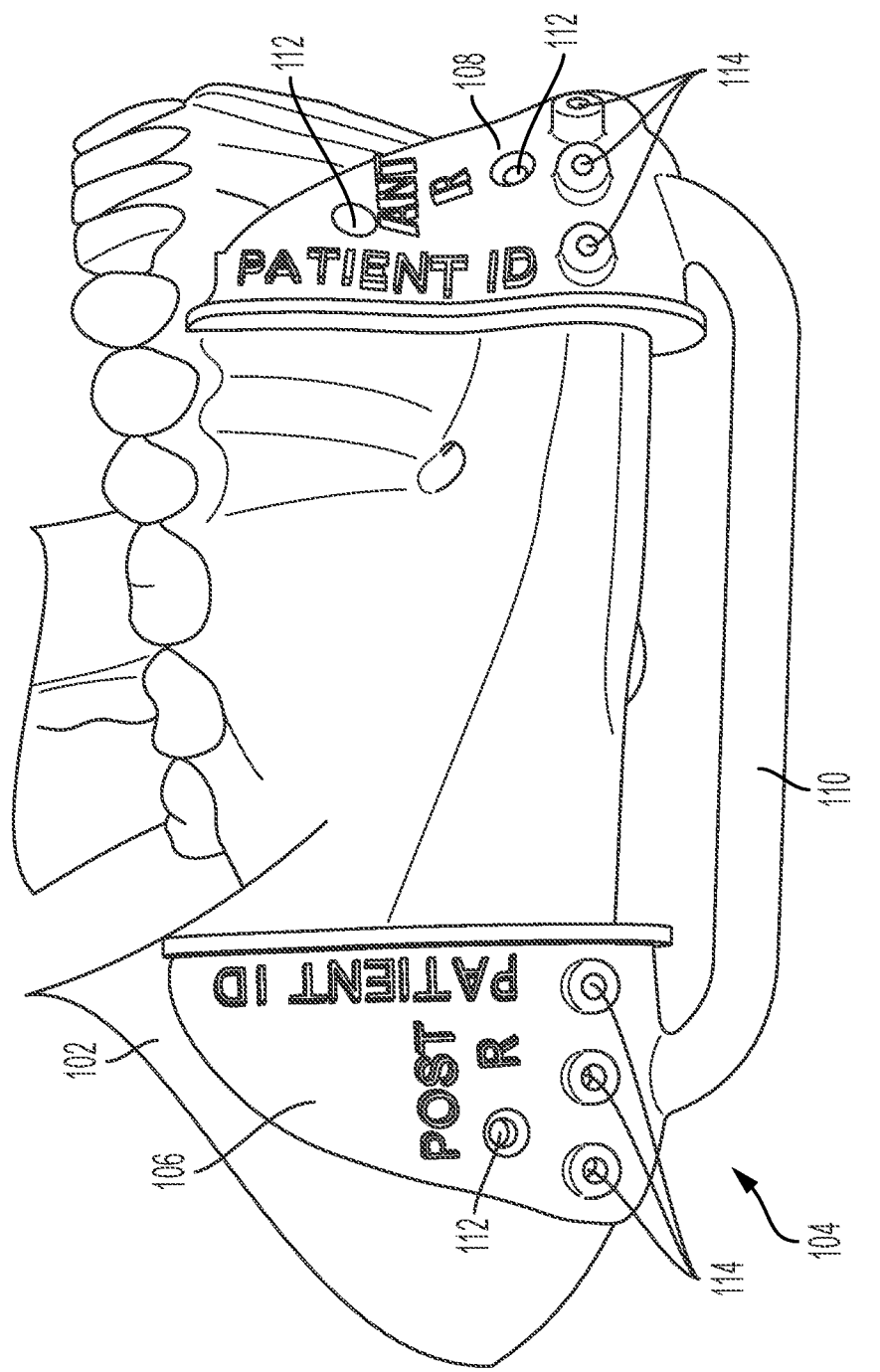
FIG. 1(a) depicts a three dimensional (3D) rendered image of a portion of a mandible bone with a prior art guide placed thereon.
Figure 1B:
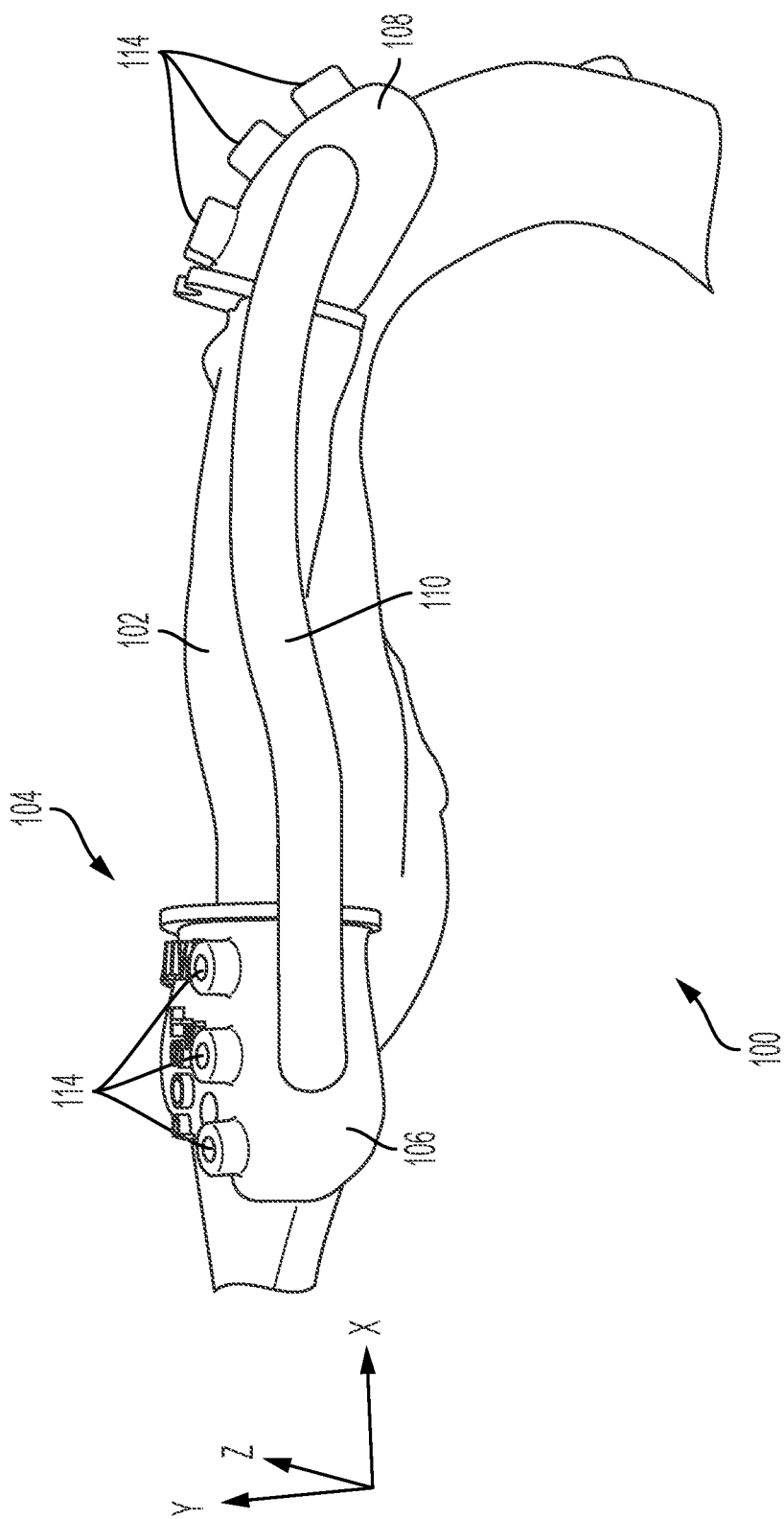
FIG. 1(b) depicts the 3D rendered image of FIG. 1(a) from a different perspective.
Figure 2A:
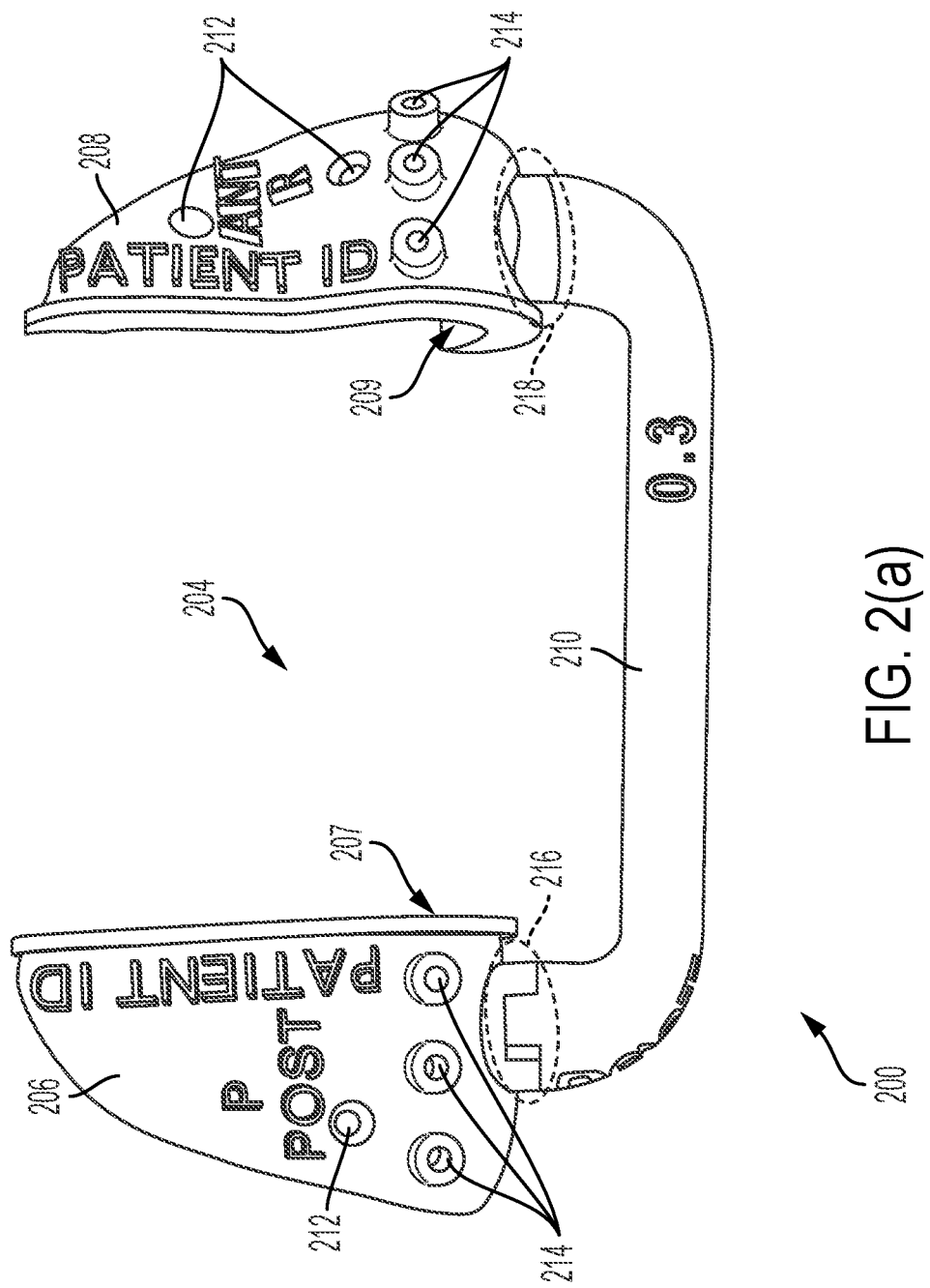
FIG. 2(a) depicts a 3D rendered image of a guide having a removable strut, in accordance with embodiments of the present disclosure.
Figure 2B:
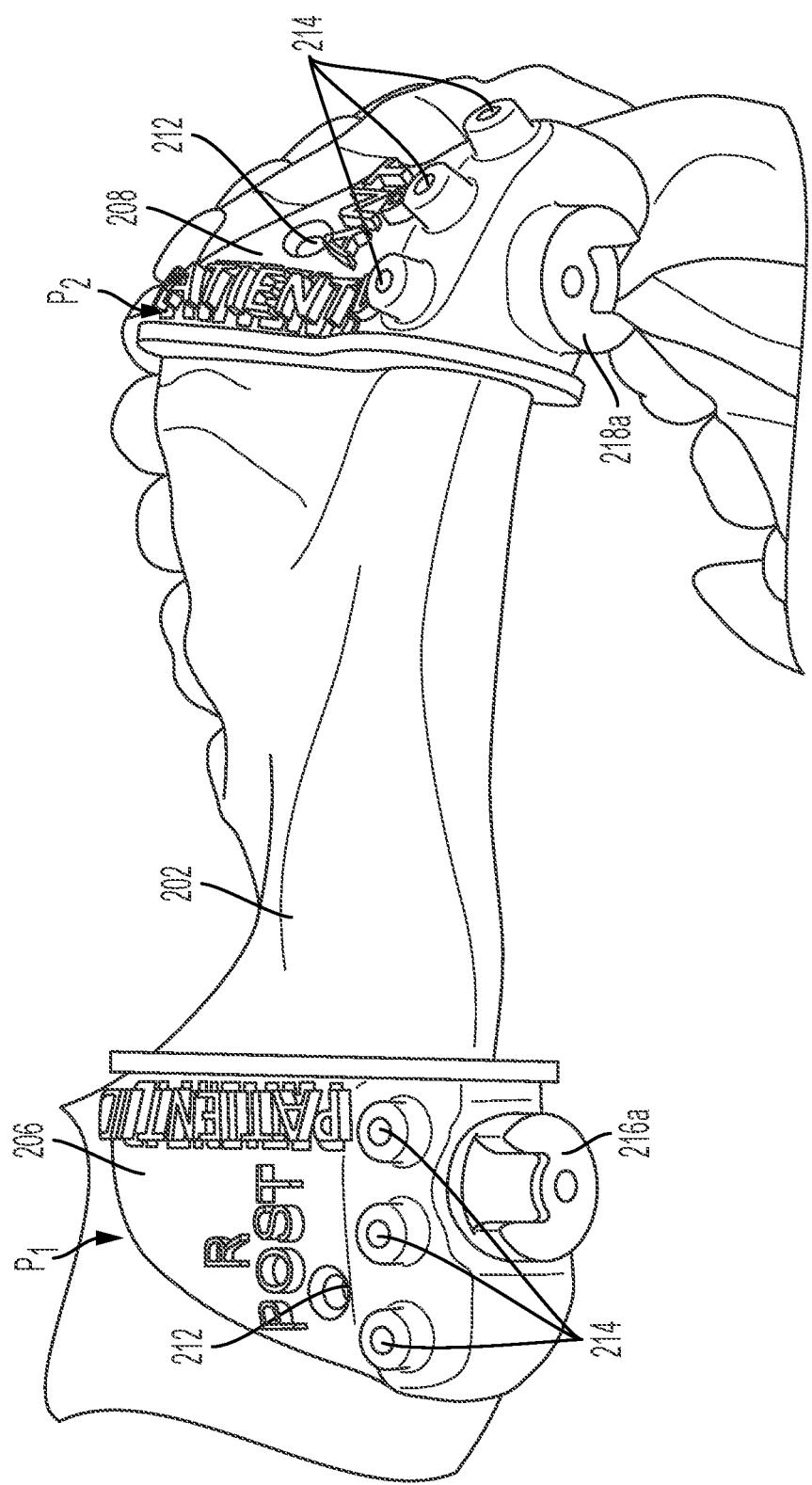
FIG. 2(b) depicts a 3D rendered image of the guide of FIG. 2(a) positioned on a biological structure without the strut, in accordance with embodiments of the present disclosure.

Referring now to FIG. 2(a), a 3D rendered image 200 of guide 204 having removable strut 210, is shown. Guide 204 includes first guide portion 206, second guide portion 208, and strut 210 that connects first and second guide portions 206 and 208, respectively. Strut 210 facilitates positioning first guide portion 206 and second guide portion 208 at first position P1 and second position P2 (respectively) on an underlying biological structure (e.g., mandible bone 202 shown in FIG. 2(b)) desired by a surgeon. First position P1 and second position P2 are, at least partially, determined by the length of strut 210. Referring back to FIG. 2(a), strut 210, in some embodiments, is also designed to resist forces that would otherwise bring first guide portion 206 and second guide portion 208 towards each other. In embodiments, both first guide portion 206 and second guide portion 208 define apertures 212 and 214 that may allow guide 204 to be secured to their respective positions on the underlying bone. One of the apertures of apertures 212 and 214 may be used as drill guides for plates that may be introduced by a surgeon at a later stage in the procedure. In embodiments, the design of the apertures that indicate drilling apertures appear different than the ones that indicate securing (or fastening) apertures. For example, the apertures that may be used for drilling do not have an elevated design (e.g., aperture 212), whereas the apertures that may be used to fasten the guide have an elevated design (e.g., aperture 214). First guide portion 206 has a contact surface 207 and second guide portion 208 has contact surface 209; both the contact surfaces 207 and 209 may be viewed as mirror images or negatives or reverse contours or contours of surfaces of mandible bone 202.

In embodiments, at least one of the guide portion 206 or 208 may be designed to 1) conform to the shape of one or more anatomical landmarks present near the bone (or portion thereof) on which the surgeon wants to operate, and 2) attach (or latch) the guide portion to the one or more anatomical landmarks. In aspects, the contact surface (or inner contour) of a guide portion (207 or 209) may be designed to follow at the contour of the one or more anatomical landmarks and the bone on which the surgeon wants to operate. In embodiments in which the guide portion is designed to attach (e.g. snugly fit) to one or more anatomical landmarks, the guide portion may be secured to the underlying bone without using any fixation devices. In embodiments, both guide portions 206 and 208 may be designed to conform and attach to anatomical landmarks near the bone on which the surgeon wants to operate. In such embodiments, both guide portions may be secured to the underlying bone without using any fixation devices. In embodiments, one guide portion (e.g., guide portion 206) may be secured with the underlying biological structure using one or more surgical fixation devices and the other guide portion (e.g., guide portion 208) may be secured with the underlying biological structure at the anatomical landmark with or without using any fixating devices.

Figure 2C:
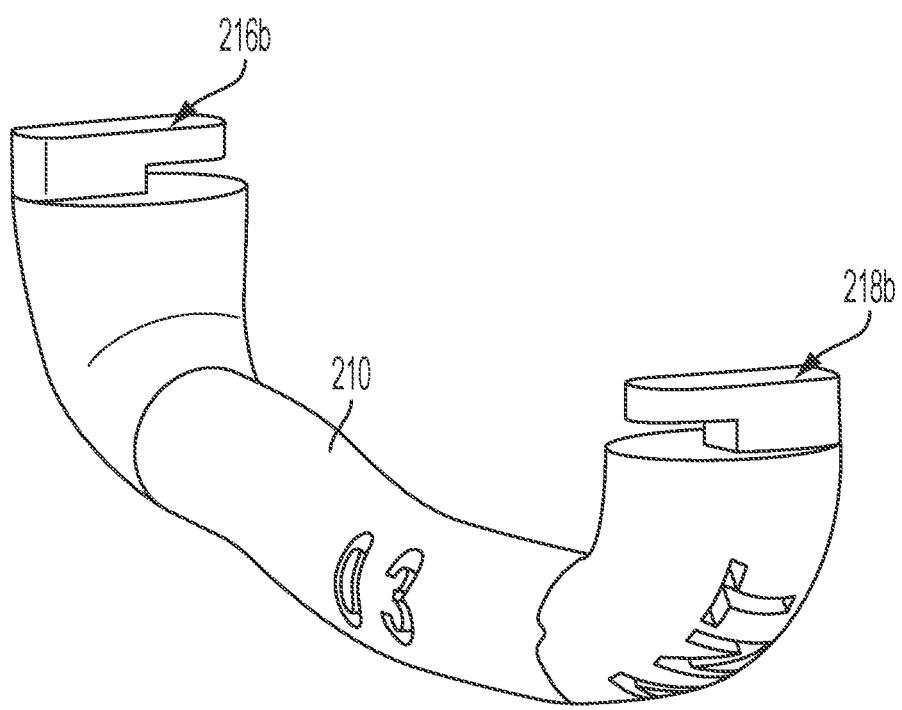
FIG. 2(c) depicts a 3D rendered image of the removable strut of FIG. 2(a), in accordance with embodiments of the present disclosure.

First portion 206 is connected to strut 210 via connection 216 and second portion 208 is connected to strut 210 via connection 218. Connections 216 and 218 are designed to allow a surgeon to connect and disconnect strut 210 from first and second portions 206 and 208, respectively. Each of the connections 216 and 218 includes two mating parts. The amount of clearance between each of the two mating parts may determine whether the parts can move independently from each other, or are temporarily joined. Referring again to FIG. 2(b), mating parts 216a and 218a that are defined in first and second portions 206 and 208, respectively are shown. Briefly referring to FIG. 2(c), strut 210 including mating parts 216b and 218b are shown. Mating parts 216b and 218b are male mating parts and are designed to fit into female mating parts 216a and 218a, respectively. In other embodiments, mating parts 216a and 218a may be male mating parts, and in that scenario, mating parts 216b and 218b would be female mating parts.

In one embodiment, the mating of the mating parts may form an interference-based connection (or fit). An interference-based connection/fit, also sometimes referred to as a friction fit, is an example fastening technique that connects two parts (e.g., first portion 206 and strut 210), via friction, after the parts are pushed together, rather than by any other means of fastening. The tightness of the connection/fit is controlled by the amount of clearance between the two mating parts. The strength of interference required to connect or disconnect the two parts may result in different types of interference connections, such as a loose connection, or light interference connection. In some embodiments, the strength depends on the type of material used to manufacture the guide, the size of the connecting parts, and the desired degree of tightness.

In order to connect strut 210 with the first and second portions 206 and 208, the surgeon may slide mating part 216b into mating part 216a, and may slide mating part 218b into mating part 218a. In order to disconnect strut 210 from the first and second portions 206 and 208, the surgeon may slide out the mating parts 216b and 218b from mating parts 216a and 218a, respectively. In some embodiments, because of the relative position of the mating parts, the surgeon may need to twist strut 210 in order to disconnect strut 210 from the first and second portions 206 and 208, respectively. Connections 216 and 218 are shown to be sliding fit/connections. However, in other embodiments, connections 216 and 218 may include other types of removable fits, such as button fit, snap fit, and the like.

During an osteotomy procedure, the contour of contact surfaces (e.g., contact surface 207 or 209) may facilitate positioning of a guide portion (e.g., guide portion 206) at a desired position, e.g., position P1. To illustrate, the imitating structure/design of the contact surface of the guide portion 206 may help ensure proper positioning and orientation (e.g., during initial placement) of the guide portion 206 at the desired position. Once the guide portion 206 is positioned, the surgeon may secure the guide portion 206 to the underlying bone (e.g., with fixation devices). In implementations in which the guide portion 206 is designed to be secure using an anatomical landmark, the guide portion 206, after latching onto the anatomical landmark, automatically positions and secures itself at the desired location at the operated bone.

The contour of the contact surface (e.g., contact surface 209) of the guide portion 208 also facilitates positioning of the guide portion 208 at its desired portion 208. In some implementations, strut 210 may also facilitate positioning of the guide portion 208 at its desired position, position P2. To illustrate, once the guide portion 206 is positioned and secured at its desired position P1, the strut 210 may be connected to the guide portion 206. Following the connection, the strut 210 extends towards the desired position (position P2) of the guide portion 208 and facilitates positioning of the guide portion 208 at P2. The surgeon may then connect the guide portion 208 to its corresponding mating portion in the strut 210 to position (and secure, e.g., using fixation devices) the guide portion 208 at P2.

Whether a guide portion, e.g., portion 206, is to be positioned and secured before being connected to the strut 210 may depend on the type of procedure or the surgeon's prerogative. Therefore, in some implementations, at least one of the guide portions 206 and 208 may be positioned and secured to the operated bone before being connected to the strut 210. On the other hand, in some implementations, at least one of the guide portions 206 and 208 may be positioned and secured to the operated bone while they are being connected to the strut 210.

This disclosure that follows describes the guides that may use different kinds of struts (e.g., different in geometrical characteristics, such as length and/or slope) having two mating portions at different instances during an osteotomy procedure. However, it should be appreciated that the disclosure that follows is not intended to be limited to using a fixed number of struts at different instances during the surgery (e.g., two struts during initial placement and two during repositioning), but is to be accorded the widest scope consistent with the principles and novel features of the guides with different kinds of removable struts, as described ahead. Thus, the description ahead is provided to enable any person skilled in the ordinary art to make or use the disclosure. Various modifications to the disclosure will be readily apparent to those skilled in the ordinary art, and the generic principles of the use and manufacturing of the guides defined herein may be applied to other variations as well (e.g., using a first set of struts including one single strut having a first geometrical characteristics during initial placement and cutting, and a set of struts including two struts having a second geometrical characteristics different from the first geometrical characteristics during repositioning of the osteotomotized bone).

Described ahead is an osteotomy procedure, Genioplasty, which is a type of osteotomy procedure typically performed on the chin bone. Genioplasty may include advancing, or moving the chin forward; pushing back, or moving the chin backward; moving the chin side-to-side to help asymmetrical chins; or vertical movement of a portion of the chin bone, such as making the chin longer or shorter. Currently, a Genioplasty procedure includes using multiple different guides, each used for a unique function. For example, a Genioplasty procedure may use two different guides, such as a cutting guide and a positioning guide, where the cutting guide facilitates resecting the chin bone, and the positioning guide facilitates positioning the resected bone to its desired place, while the surgeon performs other steps, for instance, cementing the empty portion between the resected bone and the chin. Thus, after resecting the bone using the cutting guide, the surgeon installs the positioning guide. Installing the positioning guide includes opening the mouth of the patient, removing the surgical screws used to secure the cutting guide, removing the cutting guide, and then installing the positioning guide to hold the resected bone. Removing the cutting guide and then installing the positioning guide consumes a lot of time during surgery.

Guides that are designed to include one or more removable struts may circumvent the use of different guides during a Genioplasty procedure. For example, guides designed include one or more removable struts may be designed to connect with different kinds of one or more removable struts, which may allow guides to perform more than one function during surgery.

Figure 3A:
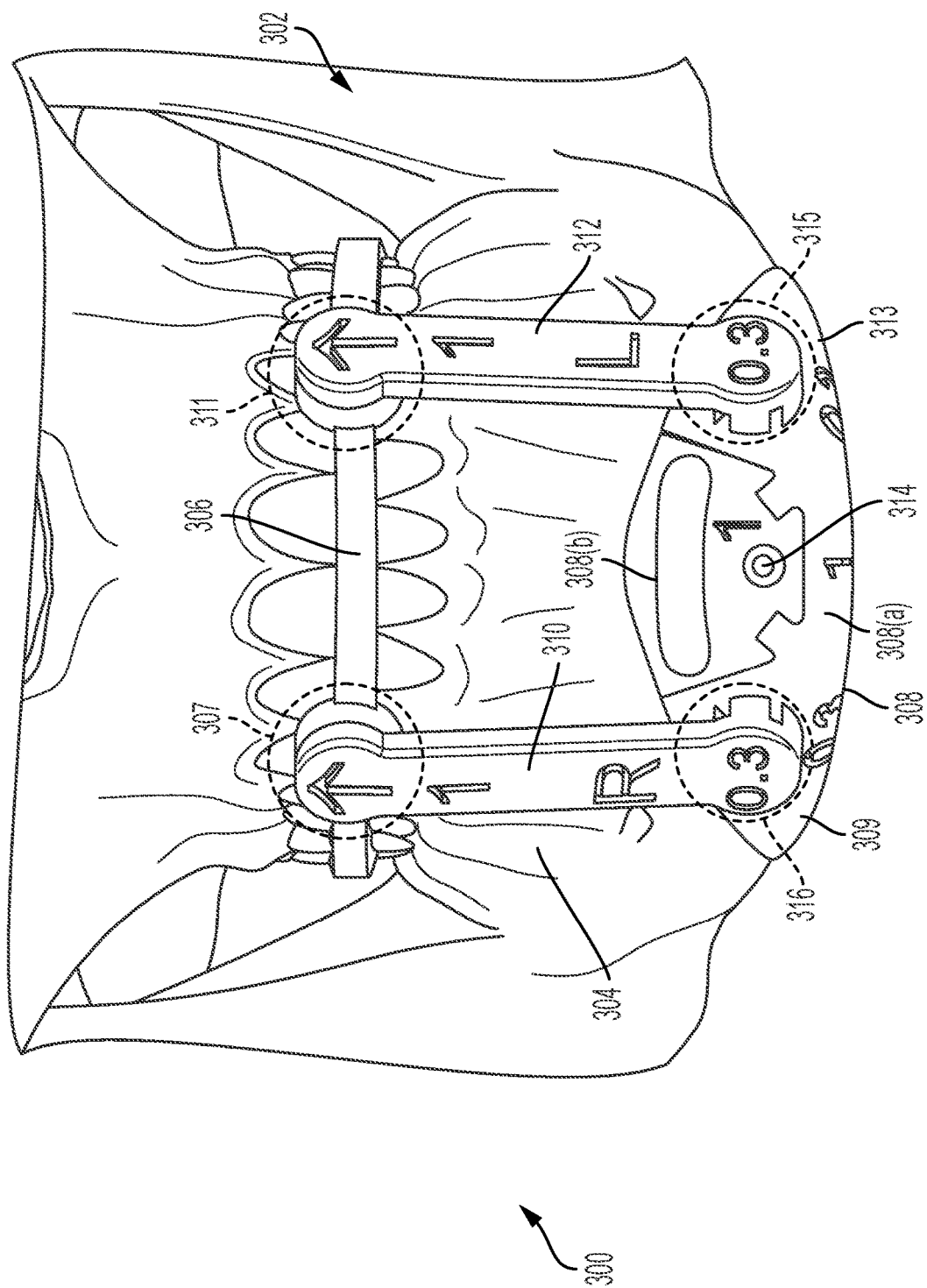
FIG. 3(a) depicts a 3D rendered image of a guide having removable struts that may be used in a Genioplasty osteotomy procedure, in accordance with embodiments of the present disclosure.

Referring to FIG. 3(a), a 3D rendered image 300 of guide 304 that may be used in Genioplasty osteotomy procedure is shown. Guide 304 includes occlusion portion 306, mental portion 308, and struts 310 and 312. Struts 310 and 312 connect occlusion and mental portions 306 and 308, respectively. Struts 310 and 312 facilitate positioning one guide portion (e.g., mental portion 308 or a portion thereof) at a desired position on the chin once the other guide portion (e.g., occlusion portion 306) is positioned and secured at its desired position. To illustrate, once the occlusion portion 306 is positioned and secured at its desired position at the occlusion location, the surgeon may connect the struts 310 and 312 to the occlusion portion 306. Following the connection, the struts 310 and 312 may extend towards the desired position (e.g., mental position) of the mental portion 308 and facilitates positioning of the mental portion 308. Struts 310 and 312, in some embodiments, may be designed to resist forces that would otherwise bring mental portion 308 towards occlusion portion 306.

Figure 3B:
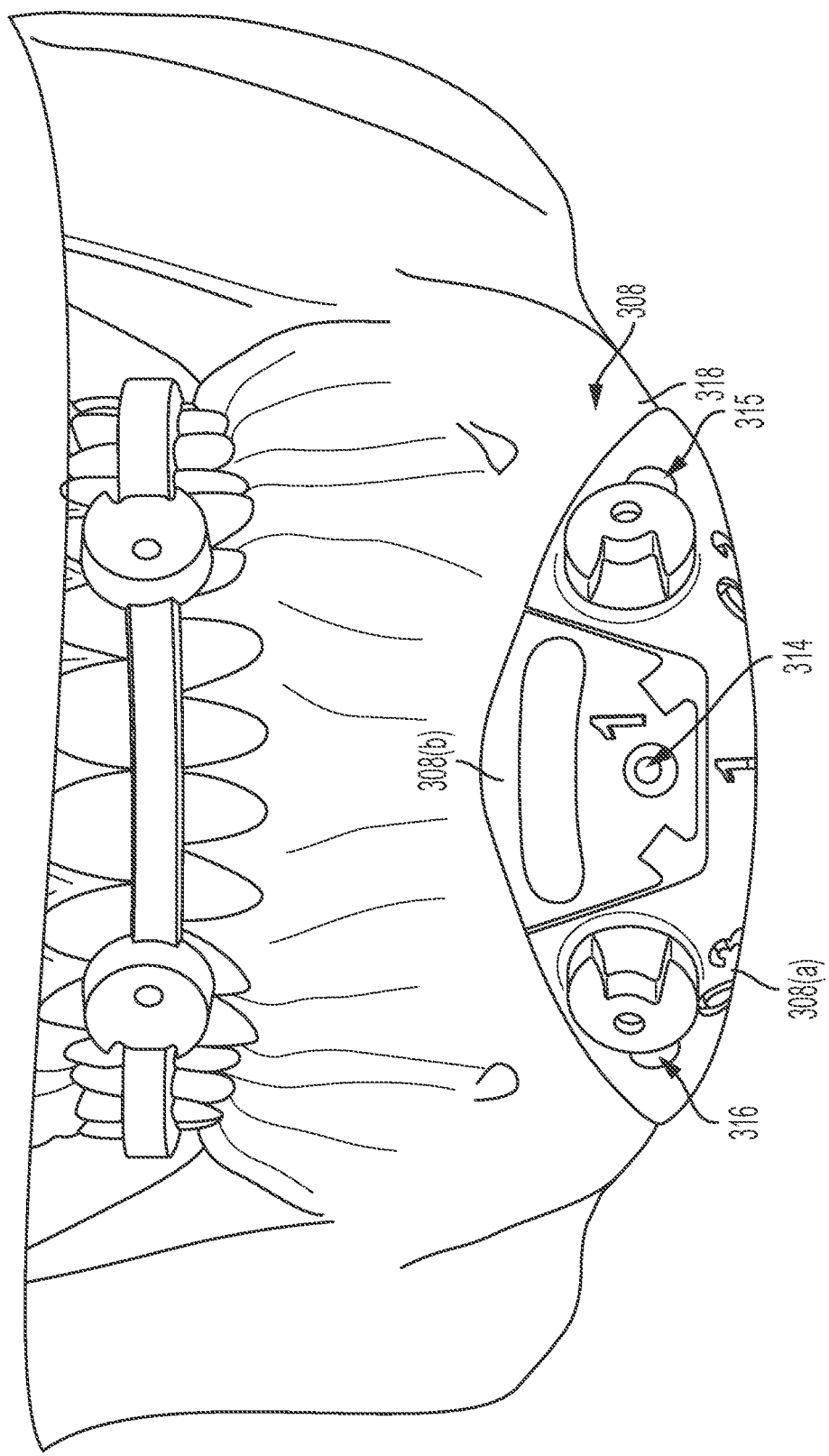
FIG. 3(b) depicts a 3D rendered image of the guide of FIG. 3(a) without the struts, in accordance with embodiments of the present disclosure.

In embodiments, a guide portion may further include different guide portions. For example, mental portion 308, in some embodiments, may further include different guide portions, such as a first portion 308(a) and a second portion 308(b). First portion 308(a) may define apertures 315 and 316 (readily visible in FIG. 3(b)) that allow first portion 308(a) to secure to the underlying bone. Second portion 308(b) may define aperture 314 that allows second portion 308(b) to secure to the underlying bone. First and second portions 308(a) and 308(b) may have contact surfaces that may be viewed as mirror images or negatives or reverse contours or contours of their respective underlying bones. During an osteotomy procedure, the contour of contact surfaces of the first and second portions 308(a) and 308(b) may facilitate positioning of the mental portion 308 at its desired position. To illustrate, the imitating structure/design of the contact surface of the first and second portions 308(a) and 308(b) may help ensure proper positioning and orientation of the mental portion 308 at its desired position.

Connections 307 and 309 connect strut 310 to occlusion portion 306 and first portion 308(a), respectively; connections 311 and 313 connect strut 312 to occlusion portion 306 and first portion 308(a), respectively. Connections 307, 309, 311, and 313 may be designed to also allow a surgeon to disconnect struts 310 and 312 from their respective underlying portions of guide 304. In some embodiments, connections 307, 309, 311, and 313 are designed to allow a surgeon to connect struts that are different from the struts 310 and 312 (e.g., different in geometrical characteristics, such as length and slope). Similar to the description of guide 204, each of the connections 307, 309, 311, and 313 may include two mating parts. The amount of clearance between each of the two mating parts may determine whether the parts can move independently from each other, or are temporarily joined. The mating parts within each of the connections 307, 309, 311, and 313 may be designed to fit into one another. For example, the mating parts inside connection 307, for instance, include a male mating part and a female mating part. Similar to the description of guide 204, the mating of mating parts of the connections 307, 309, 311, and 313 may form an interference-based connection (or fit). In other embodiments, connections 307, 309, 311, and 313 may include other forms of removable fits, such as button fit, snap fit, and the like.

Figure 3C:
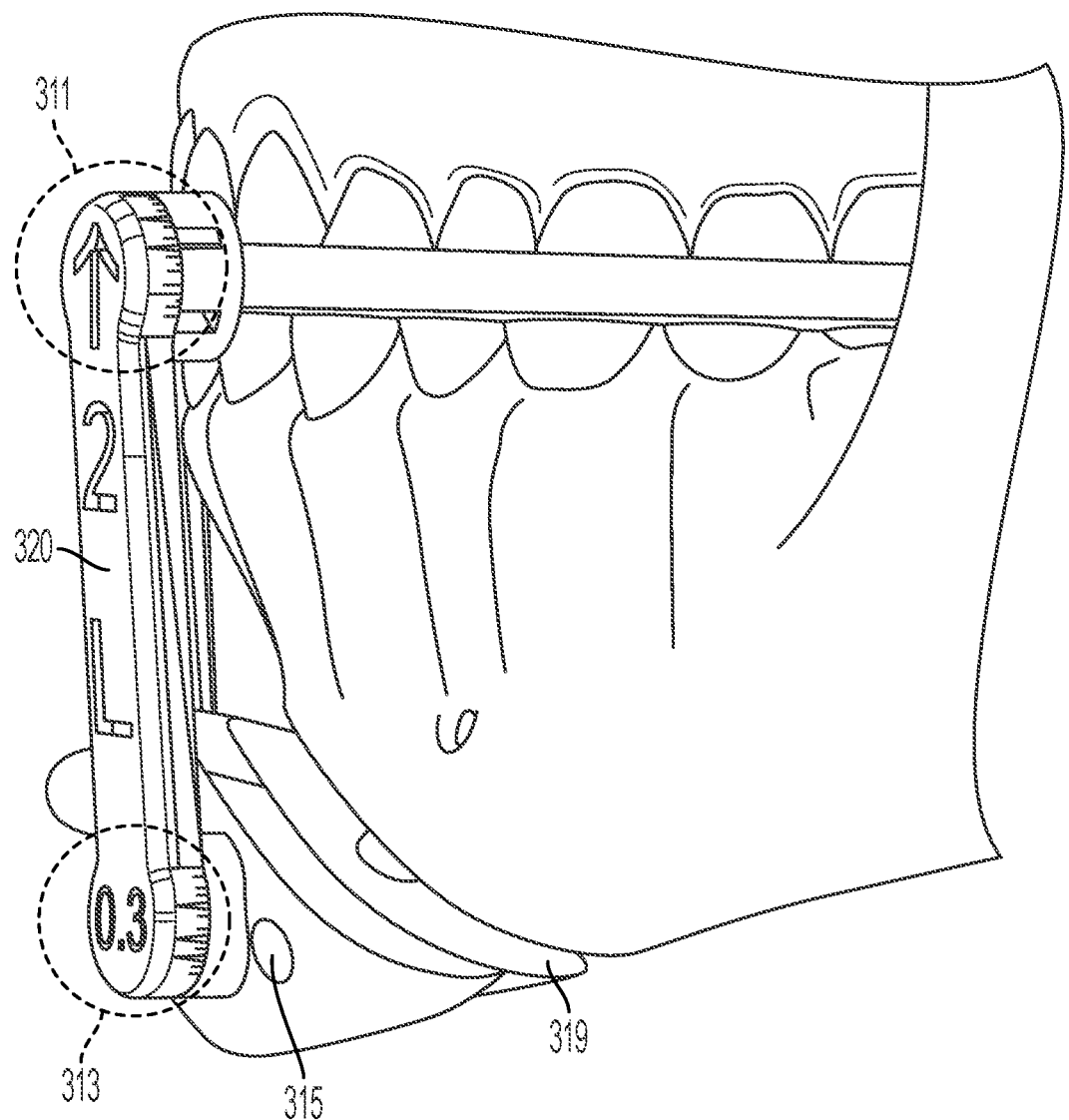
FIG. 3(c) depicts a 3D rendered image of the guide of FIG. 3(a) with a different pair of struts, in accordance with embodiments of the present disclosure.

While performing Genioplasty using guide 304, a surgeon may first open the patient's mouth and position occlusion portion 306 appropriately between the upper and lower jaws of the patient. The contour of the occlusion portion 306 may assist the surgeon in positioning and securing the occlusion portion 306 at its desired location. As noted above, struts 310 and 312 may facilitate positioning of the other guide portion (e.g., mental portion 308 or a portion thereof) at its desired location. As such, the length of struts 310 and 312 may be chosen such that it facilitates positioning a portion (e.g., first portion 308(a)) of the mental portion 308 to its desired position onto the chin. As is apparent from FIG. 3(a), first portion 308(a) and second portion 308(b) have jigsaw puzzle-like boundaries that fit with each other. Following the positioning and securing of the first portion 308(a), the surgeon then may place second portion 308(b) at its desired position on the chin bone (or mandible) to form the complete mental portion 308. The surgeon may then secure the second portion 308(b) using surgical screws/wires through apertures 314, 315, and 316. Following that, the surgeon may remove struts 310 and 312 (see FIG. 3(b)) which improves the line of sight to the boundary 318 of mental portion 308. The surgeon may then resect the underlying chin at the boundary 318. The resected bone is depicted in FIG. 3(c) as bone 319. After that the surgeon may reposition, e.g., advance, the resected bone 319 and use a different pair of struts (e.g., strut 320 of FIG. 3(c)) that have slopes and lengths different than the slopes and lengths of struts 310 and 312. The new pair of struts may be designed to hold the resected bone 319 to its final (or a newly desired position).

Figure 3D:
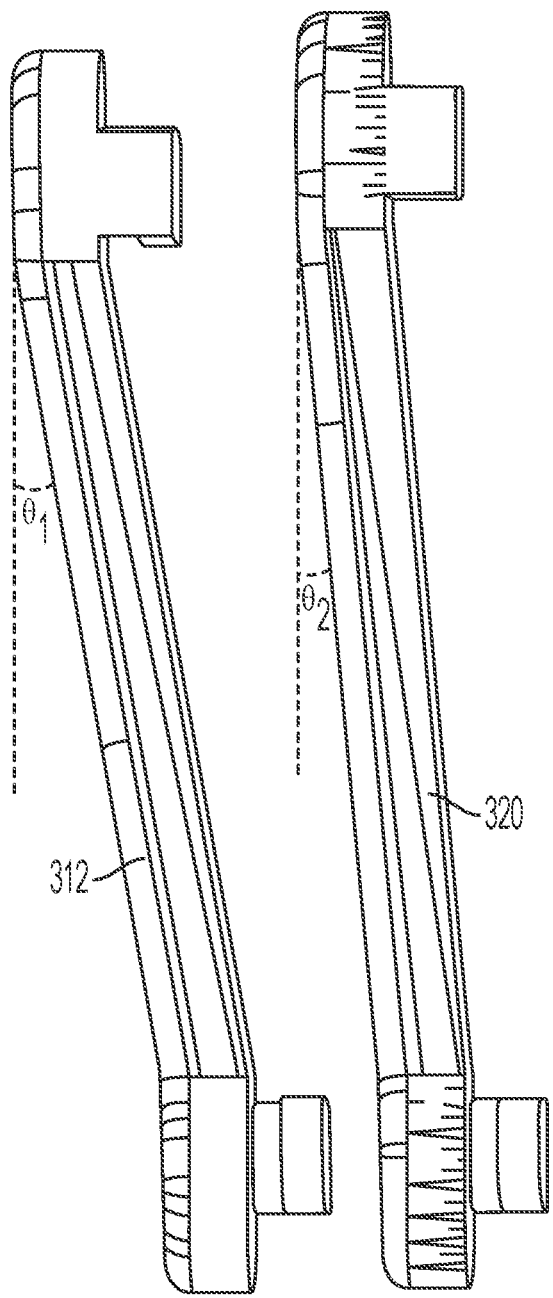
FIG. 3(d) shows an image depicting the difference in slope and lengths of different struts employed in the guide of FIGS. 3(a) and 3(c), in accordance with embodiments of the present disclosure.
Figure 3E:
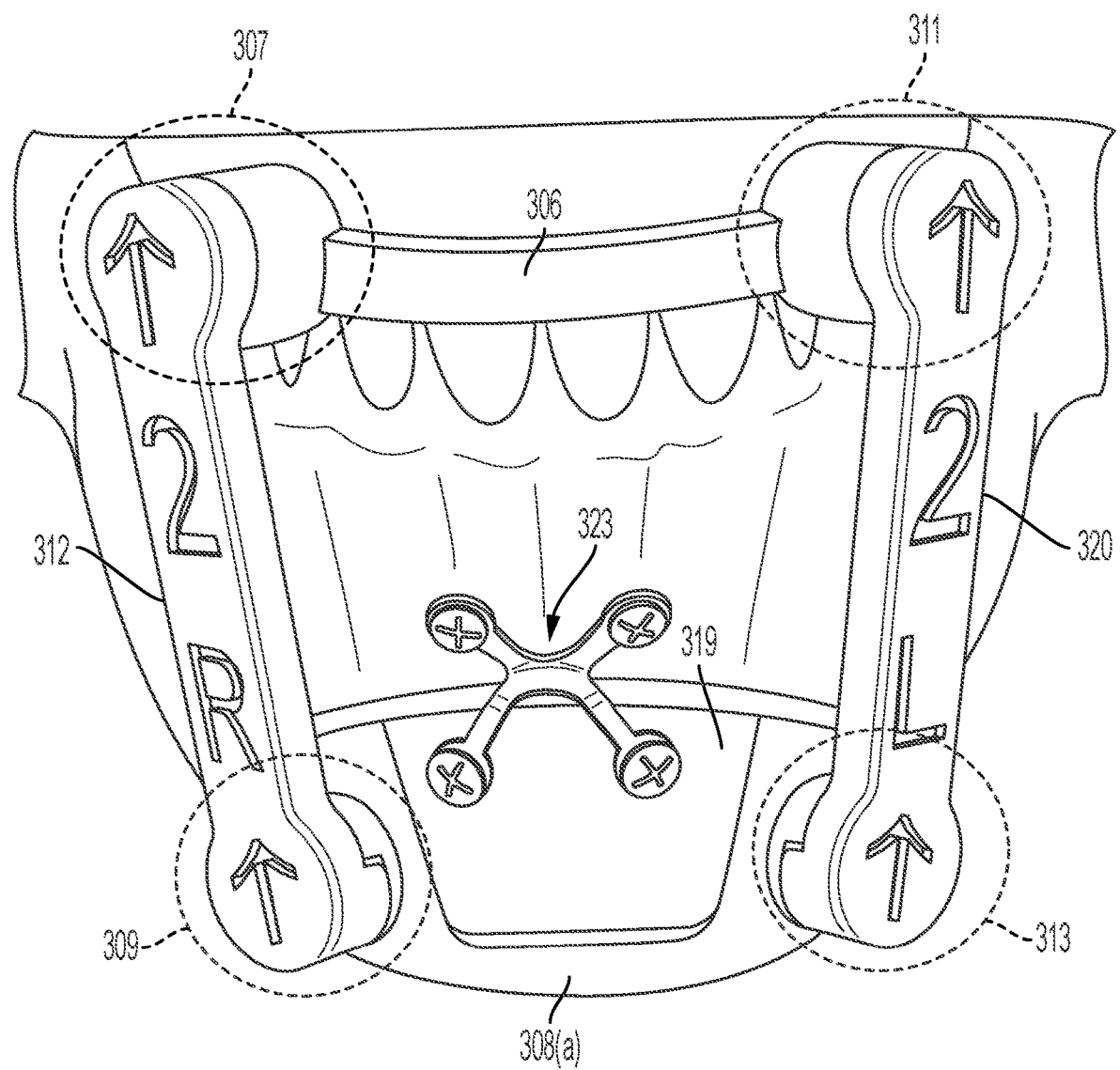
FIG. 3(e) depicts an image of the guide of FIG. 3(a) with the different pair of struts, in accordance with embodiments of the present disclosure.

Referring now to FIG. 3(e), an image depicting the new pair of struts (struts 320 and 312) that are designed to hold the resected bone 319 to its final (or desired position) is shown. As can be observed from FIG. 3(e), the surgeon may remove the second portion 308b which allows the surgeon to secure the resected bone 319 using surgical screws 323. The surgeon may then fill the empty space between the resected bone 319 and the chin using bone cement, for example, to firmly secure the resected bone 319 at the desired position. Referring to FIG. 3(d), an image depicting the difference in slope and lengths of the two pair of struts is shown. The second set of struts (e.g., strut 320) that are used to reposition the resected bone 319 have a slope that is less than the slope of the first set of struts (e.g., strut 312).

It is now readily apparent by the description above that guide 304 is designed to have removable struts, which facilitates guide 304 to perform the functions of both the cutting guide and the positioning guide. Furthermore, having removable struts prevents inaccuracies (e.g., inaccurate resection of the underlying bone) and prevents the waste of valuable surgery time incurred by first installing the cutting guide and then replacing it with a positioning guide.

Figure 4:
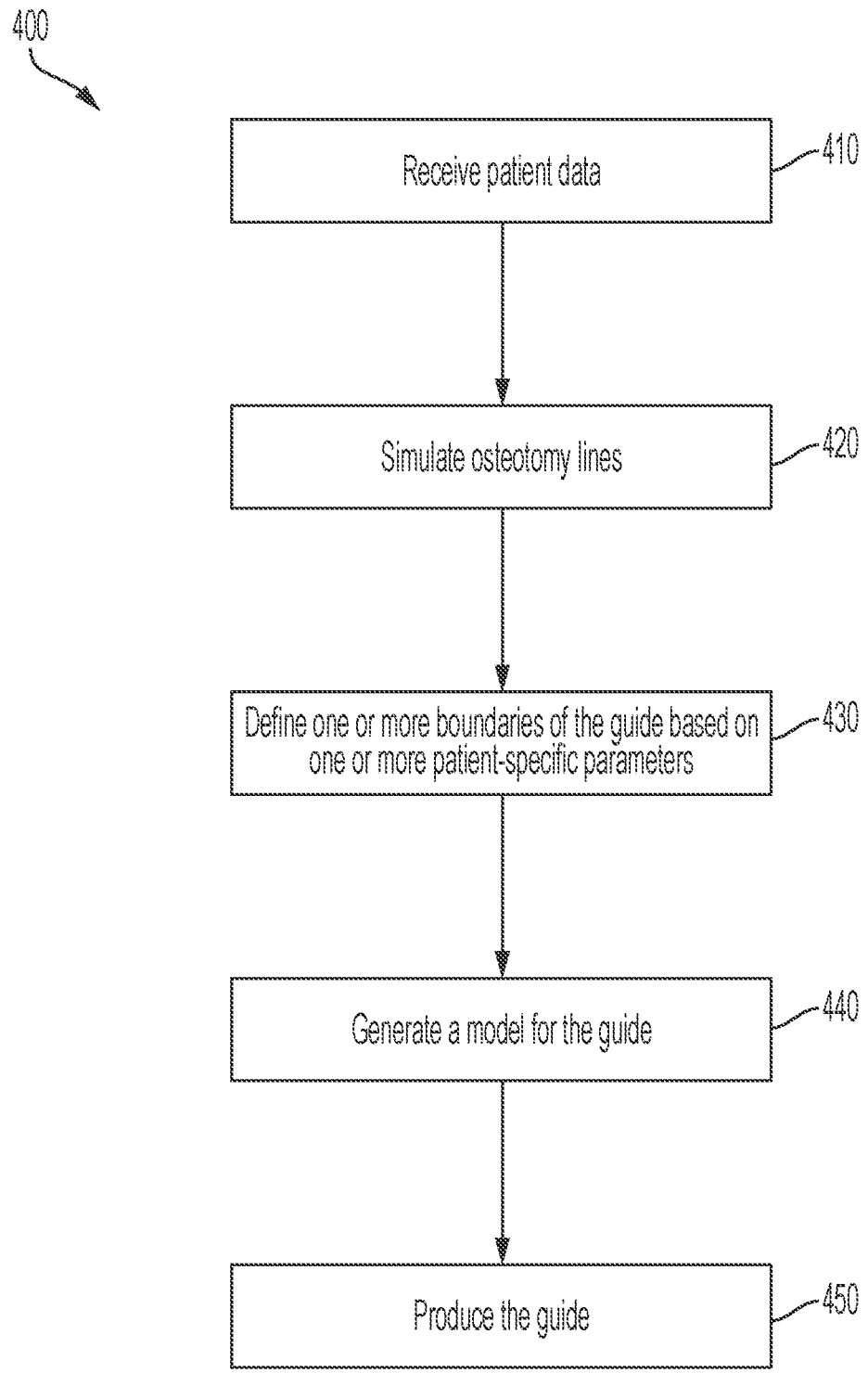
FIG. 4 depicts an illustrative method that may be used to design and manufacture the aforementioned guides, in accordance with embodiments of the present disclosure.

Referring now to FIG. 4, an illustrative method 400 that may be used to design and manufacture the aforementioned guides with removable struts is shown. In some cases, method 400 may be performed, without limitation, by a medical institution (e.g., a hospital) where the surgery will eventually take place. In other cases, method 400 may be performed by a contracted third party (e.g., a medical device company) that works with the medical institution to generate and manufacture the guides.

In some embodiments, the guides may be patient-specific. The patient's data may be received by a computer system and stored in a computer-readable medium in the computer system. In those embodiments, method 400 begins with block 410 that includes receiving the patient's data. Patient-specific information is advantageously used to ensure that the guides appropriately conform to the surface of the underlying biological structure. Patient-specific information, in some examples, includes one or more electronic images and/or measurements of the surface of the desired biological structure. Images and measurements of the surface of the biological structure, in one example, may provide coordinates that define the surface and shape of the biological structure. The electronic images of the tissue may be from, without limitation, a CT image, a spiral CT image, an MM image, an ultrasound scan, digital tomosynthesis, or optical coherence tomography. In some embodiments, the coordinates of the biological structure may be utilized to shape at least some of the portions of the guide. The received patient data, in one embodiment, may then be utilized to generate a 3D bone model of the portion of the body. The 3D bone model may then be subsequently used in surgical planning by the surgeon performing the procedure. The 3D bone model, in one embodiment, is generated using a computer system configured to receive the images and/or other details and generate the bone model using a software system installed in the computer system.

Method 400 may then move to block 420 that includes simulating, in the computer system, osteotomy lines on the 3D bone model of the patient. In one embodiment, a user (e.g., medical device technician) defines the cutting planes of the bone on which the surgeon wants to operate. In some cases, the surgeon may first virtually operate on the desired bone; the virtual operation may include the surgeon virtually disconnecting at least one of the struts from the virtual guide. In some embodiments, the user may choose the type of fit (e.g., interference fit, snap fit, and the like) that may be used to design the removable connections based on a feedback received by the user during the virtual operation.

Once the optimal type of fit and the desired portion of the bone are identified, the method 400 may then move to block 430 that includes generating the guide that will be used by the surgeon during the procedure. In some embodiments, the block 430 includes defining one or more boundaries of a guide. The boundaries of the guide, in some embodiments, are based on one or more input parameters, which may be provided by the surgeon. In some embodiments, the user of block 410 extrapolates relevant input parameters from the images and/or other details received in block 410.

After defining the boundaries, at block 440, the user may instruct the computer system to generate a 3D model for the guide. This 3D model may then be used to manufacture and produce the guide (block 450). In some cases, the 3D model may first sent to the surgeon for his approval, and following his approval, a guide is manufactured. In one embodiment, the guide is manufactured using additive technology or freeform fabrication. In this method of manufacture, the guides are formed through successive fusion of chosen parts of powder layers applied to a worktable. In some embodiments, PA 12 (also known as Nylon 12) is used as the powder. The guides formed using PA 12 have high tensile strength, impact strength, and are able to flex without fracture. In other embodiment, other types of material may be used. In summary, once the patient-specific information is ascertained, rapid prototyping or other manufacturing techniques may be used to adapt the guide to the patient's particular biological structure. In some embodiments, a mold may be made to form the guide. In some embodiments, a guide may be manufactured using a 3D printing technology disclosed in co-pending U.S. patent application Ser. No.

16/378,446, entitled System and Method for Forming Material Layers for Surgical Applications, and filed by the assignee of the present application on Apr. 8, 2019. The disclosure of U.S. patent application Ser. No. 16/378,446 is incorporated by reference herein in its entirety.

The guide manufactured using the techniques described above may be disposed in a packaging unit (also referred to as surgical kit). The packaging unit may include a contoured unit having a contoured surface that matches a contour of the biological structure (e.g., bone, such as maxilla bone) on which a surgeon would operate. The contoured unit may be 3D printed of metal, plastic, poly-ether-ether-ketone (PEEK) material, etc. in a same or similar manner as described in U.S. patent application Ser. No. 16/378,446. As such, a guide may be disposed onto the contoured unit and provide a visual aid to the surgeon before the surgery. In some embodiments, the contoured unit also has one or more features that would further facilitate the surgery by providing a visual aid to the surgeon. For example, the contoured unit may have one or more features, such as apertures, which may be holes for receiving surgical screws that are selected based on thickness/depth of bone exhibiting the contour in the 3D model of the desired bone of a patient. Additionally, the contoured unit may be a part of a surgical kit that includes other medical devices (e.g., bone plates) that may be used during the surgery. In some embodiments, the packing unit includes a lid that may have a reverse contour, which is designed to mate with the contour of the surface of the contoured unit in such a way that the contoured unit and the guide(s) and/or other medical devices (e.g., bone plates and surgical screws) are secured in place when the lid is connected to the contoured unit.

As an example, the surgical unit may include a first guide portion (e.g., guide portion 206 or 306) having a first mating portion (e.g., 216a) and a first contact surface (e.g., 207). In embodiments, the first contact surface may match a first contoured surface of the surgical kit, which further matches a contour of the biological structure (e.g., bone, such as maxilla bone) on which a surgeon would operate. The surgical kit may also include a second guide portion (e.g., guide portion 208 or 308) having a second mating portion (e.g., 218a) and second contact surface (e.g., 209). In embodiments, the second contact surface may match a second contoured surface of the surgical kit, which further matches another contour of the biological structure (e.g., bone, such as maxilla bone) on which a surgeon would operate. In embodiments, the surgical kit may further include a first strut having a first set of mating portions that are designed to couple with the mating portions of the above-mentioned guide portions. In embodiments, the first strut may be positioned on a third contoured surface of the surgical kit. In embodiments, the surgical kit may further include a second strut having a second set of mating portions that are also designed to couple with the first and second mating portions. To illustrate, the surgical kit may include struts of different kinds (e.g., first and second struts) that allow the guide to function as both cutting and positioning guides, as described above. In embodiments, the second strut may be positioned on a fourth contoured surface of the surgical kit. The third and fourth contoured surfaces may also different from each other with regards to their geometric characteristics (e.g., length and/or slope). Because the contoured surfaces of the surgical kit are to provide a visual aid to the surgeon before the surgery, in embodiments, the third contoured surface—which hosts the first strut—is between the first contoured surface—which hosts the first guide portion—and the second contoured surface—which hosts the second guide portion. Further, various contoured surfaces of the kit (e.g., the first and second contoured surfaces) may be designed based at least in part on the contour of a biological structure derived using magnetic resonance image (MM) of the biological structure.

Embodiments described above provide for patient-specific guides. In some cases, embodiments described above may provide for guides which are not patient-specific, meaning that the guides are not designed for a specific patient, but are designed in accordance with generic human anatomical features. Thus, the same design can be used to produce multiple guides, which can further be used during osteotomy procedures of different patients. In some embodiments, these non-patient-specific guides may be designed based on age, gender, or generic physical makeup of the human anatomical structure. As such, the non-patient-specific guides may come in different sizes, e.g., small-male, small-female, medium-male, medium-female, large-male, and large-female. By way of example, a medium-male design may be used during an osteotomy procedure of a 5 foot 6 inch, 30 year old man, whereas, a large-male design may be used during an osteotomy procedure of a 6 foot, 30 year old man.

Figure 5:
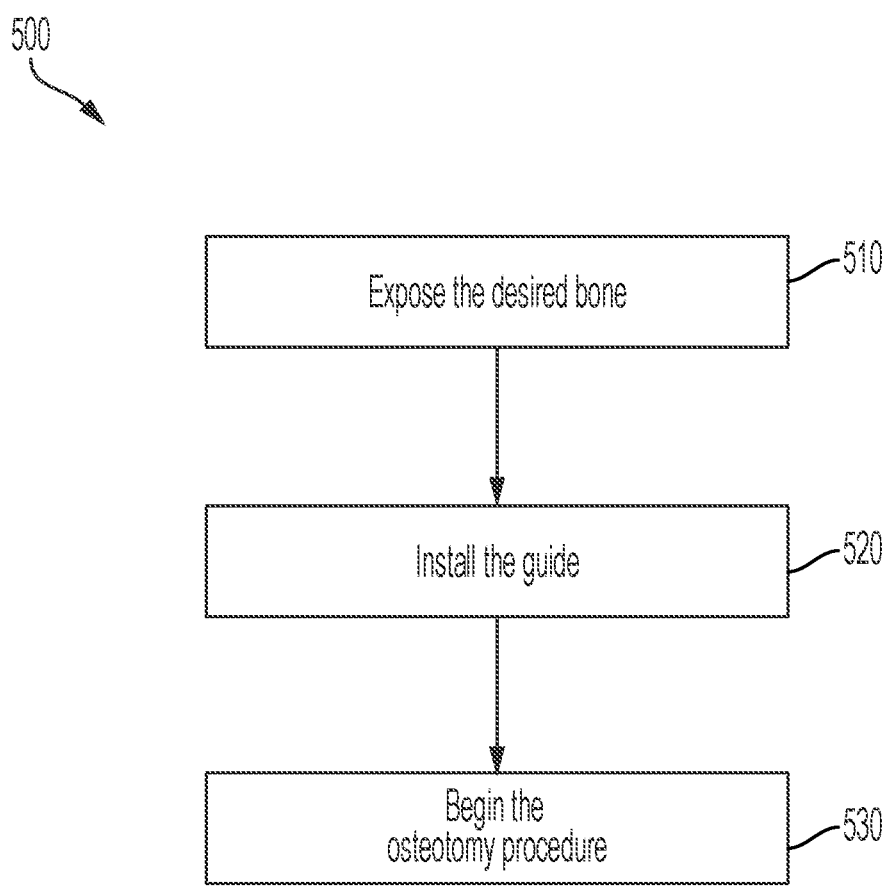
FIG. 5 depicts an illustrative method that may be implemented by a surgeon using the guide of FIG. 2(a), in accordance with embodiments of the present disclosure.

Refer now to FIG. 5, which depicts an illustrative method 500 that may be implemented by a surgeon using guide 204 described above during an osteotomy procedure. In one embodiment, method 500 begins with block 510 that includes exposing the desired bone by using relevant surgical techniques. The method 500 may then move to block 520 that includes installing guide 204. In some embodiments, installing guide 204 includes securing one or more portions of the guide using surgical screws and/or wires. In some examples, while installing guide 204, at least one portion of guide 204 may be placed at an anatomical landmark. In such cases, the surgeon may secure guide 204 using surgical screws and/or wires at only one portion as the other portion is secured without any surgical screws and/or wires around the anatomical landmark. In some cases, the surgeon may determine that the guide needs to be secured using wires or screws at the portion which is secured around the anatomical landmark. The anatomical landmark referred to in the instant application is the same or similar anatomical landmark as described in U.S. patent application Ser. No. 17/006,603 entitled "Surgical Cutting Guides Designed for Anatomical Landmarks," and filed by the assignee of the present application on Aug. 28, 2020. The disclosure of U.S. patent application Ser. No. 17/006,603 is incorporated by reference herein in its entirety. Once guide 204 is installed, the method 500 may move to the block 530 that includes beginning the osteotomy procedure. Based on the type of procedure, the osteotomy procedure may include different steps. For example, if the osteotomy procedure is performed on mandible 202 of FIG. 2(b), the surgeon, after installing guide 204, may disconnect strut 210 to have an uninterrupted view of the underlying mandible 202 and resect the mandible as desired.

As noted above, the guides may be patient-specific, and the patient's data may be received by a computer system and stored in a computer-readable medium in the computer system. A method of manufacturing a guide at least partially using the patient's data stored in computer-readable medium is now described. The method of manufacturing may include accessing a computer-readable medium having stored thereon one or more three-dimensional (3D) images of a guide and fabricating the guide based on the one or more 3D images. In embodiments, the fabricating the guide may include fabricating a first guide portion (e.g., guide portion 206 or 306) having a first mating portion (e.g., 216a or the mating portion corresponding to guide portion 306 present in connection 307) and a first contact surface (e.g., 207). In embodiments, the first contact surface matches a first contour of the underlying biological structure. In embodiments, the fabricating the guide may further include fabricating a second guide portion (e.g., guide portion 208 or 308) having a second mating portion (e.g., 218a or the mating portion corresponding to guide portion 308 present in connection 311) and second contact surface (e.g., 209). In embodiments, the second contact surface matches a second contour of the underlying biological structure. In embodiments, the fabricating the guide may include fabricating a first strut (e.g., strut 210 or 310) having a first set of mating portions that are designed to couple with the first and second mating portions. In embodiments, the first set of mating portions are designed to couple and decouple with the first and second mating portions upon application of a force at a first instance. In embodiments, the fabricating the guide may include fabricating a second strut (e.g., the strut that replaces strut 310 while repositioning the resected segment) having a second set of mating portions that are designed to couple with the first and second mating portions. In embodiments, the second set of mating portions are designed to couple and decouple with the first and second mating portions upon application of a force at a second instance.

Although embodiments of the present application and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. Moreover, the scope of the present application is not intended to be limited to the particular embodiments of the process, machine, manufacture, composition of matter, means, methods and steps described in the specification.

The invention claimed is:

1. A surgical guide, comprising:
a first guide portion having a first contact surface with a first contour and a first mating portion;
a second guide portion having a second contact surface with a second contour and a second mating portion;
a first strut having a third mating portion designed to fit in the first mating portion and a fourth mating portion designed to fit in the second mating portion, wherein the first strut is removable by disengaging the first strut with respective mating portions of the first and second guide portions,
a second strut having a fifth mating portion and a sixth mating portion, wherein the fifth mating portion is designed to fit in the first mating portion and the sixth mating portion is designed to fit in the second mating portion, and wherein the second strut is removable by disengaging the second strut with respective mating portions of the first and second guide portions,
wherein the first strut has a first slope and the second strut has a second slope, and wherein the first slope is different from the second slope.

2. The surgical guide of claim further comprising one or more apertures defined on the second guide portion.

3. The surgical guide of claim 2, wherein the first contour is configured to match a contour of a first portion of a biological structure, and wherein the second contour is configured to match a contour of a second portion of the biological structure.

4. The surgical cutting guide of claim 1, wherein the second contour is designed to at least partially extend around a portion of an anatomical landmark.

5. The surgical cutting guide of claim 1, further comprising a third strut having a seventh mating portion and an eighth mating portion, wherein the first guide further includes a ninth mating portion designed to fit in the seventh mating portion, and wherein the second guide further includes a tenth mating portion designed to fit in the eighth mating portion.

6. The surgical guide of claim 1, wherein the second guide portion comprises:
a first portion; and
a second portion configured to removably couple with the first portion.

7. The surgical guide of claim 6, wherein the second mating portion is disposed in the first portion.

8. The surgical guide of claim 6, wherein the first portion and the second portion have jigsaw shape boundaries that are configured to fit with each other.

9. The surgical guide of claim 6, wherein the first portion includes a cut away portion configured to receive the second portion.

10. The surgical guide of claim 1, wherein the first slope of the first strut is greater than the second slope of the second strut.

11. A medical apparatus, comprising:
a guide three-dimensionally (3D) printed based on different contours of a biological structure, wherein the guide comprises:
a first guide portion having a first mating portion and a first contact surface, the first contact surface is configured to match a first contour of the biological structure;
a second guide portion having a second mating portion and a second contact surface, the second contact surface is configured to match a second contour of the biological structure;
a first strut having a first set of mating portions that are designed to couple with the first and second mating portions, wherein the first set of mating portions are designed to couple and decouple with the first and second mating portions upon application of a force at a first instance,
a second strut having a second set of mating portions that are designed to couple with the first and second mating portions, wherein the second set of mating portions are designed to couple and decouple with the first and second mating portions upon application of a force at a second instance,
wherein the first strut has a first slope and the second strut has a second slope, and wherein the first slope is different from the second slope.

12. The medical apparatus of claim 11, wherein the first strut has a first length and the second strut has a second length, wherein the first length is different from the second length.

13. The medical apparatus of claim 11, wherein the first and second contour surfaces are different from one another.

14. The medical apparatus of claim 11, wherein both the first and second guide portions include one or more apertures designed to secure the first and second guide portions on the biological structure.

15. The medical apparatus of claim 11, wherein the first contour is designed to at least partially extend around a portion of an anatomical landmark in order to secure the first guide portion with the biological structure.

16. The medical apparatus of claim 11, wherein the second guide portion comprises:
   a first portion; and
   a second portion configured to removably couple with the first portion.

17. The medical apparatus of claim 16, wherein the second mating portion is disposed in the first portion.

18. The medical apparatus of claim 16, wherein the first portion and the second portion have jigsaw shape boundaries that are configured to fit with each other.

19. The medical apparatus of claim 16, wherein the first portion includes a cut away portion configured to receive the second portion.

20. The medical apparatus of claim 11, wherein the first slope of the first strut is greater than the second slope of the second strut.

* * * * *